United States Patent
Homma et al.

(10) Patent No.: US 9,050,272 B1
(45) Date of Patent: Jun. 9, 2015

(54) NAIL POLISH COMPOSITION

(71) Applicants: Michael Mitsuo Homma, Katy, TX (US); Victor Masaru Homma, West Valley City, UT (US)

(72) Inventors: Michael Mitsuo Homma, Katy, TX (US); Victor Masaru Homma, West Valley City, UT (US)

( * ) Notice: Subject to any disclaimer, the term of this patent is extended or adjusted under 35 U.S.C. 154(b) by 0 days.

(21) Appl. No.: 14/299,510

(22) Filed: Jun. 9, 2014

Related U.S. Application Data

(63) Continuation-in-part of application No. 13/694,527, filed on Dec. 10, 2012.

(60) Provisional application No. 61/569,017, filed on Dec. 9, 2011.

(51) Int. Cl.
*A61K 8/30* (2006.01)
*A61Q 3/02* (2006.01)
*A61K 8/81* (2006.01)

(52) U.S. Cl.
CPC ............ *A61K 8/8152* (2013.01); *A61Q 3/02* (2013.01)

(58) Field of Classification Search
None
See application file for complete search history.

(56) References Cited

U.S. PATENT DOCUMENTS

2006/0216250 A1* 9/2006 Schultz et al. ............... 424/59
2007/0231281 A1 10/2007 Socci

OTHER PUBLICATIONS

Material Safety Data Sheet for Elvacite Acrylic Resin—Poly(MMA/LMA) Based, Jan. 19, 2010.

\* cited by examiner

*Primary Examiner* — Michael B Pallay
(74) *Attorney, Agent, or Firm* — Buskop Law Group, PC; Wendy Buskop

(57) ABSTRACT

A nail polish composition having a crosslinked acrylic copolymer blend, a film forming plasticizing mixture, wherein a plasticizer enters into interstices of an acrylic copolymer nitrocellulose matrix modifying the flexibility of the acrylic copolymer nitrocellulose matrix, and a two component solvent. The three parts are the nail polish blend are blended to produce a nail polish composition that when applied to a nail or is applied to wet layers of other nail polish, dries all layers simultaneously producing a nail polish that dries in 1 to 2 minutes at ambient temperatures and pressures and has chip resistance and cracking resistance for at least 2 to 3 weeks of normal wear.

15 Claims, No Drawings

NAIL POLISH COMPOSITION

CROSS REFERENCE TO RELATED APPLICATIONS

The present application is a Continuation in Part of co-pending U.S. patent application Ser. No. 13/694,527 filed on Dec. 10, 2012, entitled "Long Lasting Fingernail Lacquer and Method for Manufacture," which claims priority and the benefit of U.S. Provisional Patent Application Ser. No. 61/569,017 filed on Dec. 9, 2011, entitled "Long Lasting Fingernail Lacquer and Method for Manufacture." These references are hereby incorporated in their entirety.

FIELD

The present embodiments generally relate to fast drying films which are useful as cosmetic agents or therapeutic agents as well as methods of their use.

BACKGROUND

A need exists for fast drying films which, when applied to mammalian nails, such as human nails, exhibit extremely long wear, leave a very shiny surface, can be removed with ordinary fingernail polish remover quickly, dry very fast, and do not require UV light to cure.

A further need exists for this to be something that can be done at home and does not require a trip to the nail salon.

The present embodiments meet these needs.

DETAILED DESCRIPTION OF THE EMBODIMENTS

Before explaining the present composition in detail, it is to be understood that the composition is not limited to the particular embodiments and that it can be practiced or carried out in various ways.

In the field of fingernail lacquers and fingernail coatings, prior art inventions met one or more of the above requirements but not all. For example, the prior art would have a glossy shine but would dry very slowly. Other prior art such as UV gels would dry quickly with a high gloss and be very long lasting, but would not come off without soaking in acetone for up to 10 minutes or mechanically grinding off the coating and require exposing the client to a UV light in order to cure the gel. Prior art that was fast drying would not last long and the shine would be much less glossy than the UV gels or slower drying high gloss coatings. The unique combination of quick drying able to be removed with common acetone based nail polish remover, very long lasting, does not require UV light to harden, and had a very glossy shine was not achievable with any of the prior art embodiments.

Previous coatings included standard nitrocellulose based nail lacquers. These lacquers dry very slowly and do not last very long, but can leave a very glossy finish. These formulations typically contain nitrocellulose, acrylic co-polymers, iso-propyl alcohol, ethyl acetate, butyl acetate, plasticizer agents and viscosity modifiers.

Previous coatings included fast drying fingernail lacquers and polishes which sacrifice high gloss and longer lasting for quick drying. Typical formulations consist of higher concentrations of quick drying solvents such as ethyl acetate and less of an acrylic co-polymer component. These modifications cause the coating to dry faster, though with these ingredients, the coating is less shiny and does not have long lasting behavior.

Thus, there is a need for a quick drying, long lasting fingernail coating that has a high level of shine, does not chip or come off easily, and can be removed with ordinary fingernail polish remover in a short period of time.

The invention provides a three part nail polish blend having an acrylic copolymer blend as the first component, a two part solvent formulation as the second component and a film forming plasticizing mixture as the third component.

The composition can be added to current nail polish compositions, wherein the nail polish composition has about 0.5 weight percent to about 10 weight percent (w/w) of the acrylic polymer. The inventive compositions can be applied to fingernails.

The invention is directed to new formulations for fingernail lacquer and fingernail topcoats where combining a solution of a dodecyl methacrylate-methyl methacrylate polymer having the chemical formula $C_{21}H_{38}O_4$, such as, ELVACITE® 2552 acrylic co-polymer and ethyl acetate, to standard high gloss fingernail topcoat or fingernail lacquer creates a mixture that contains from about 0.5 weight percent to about 10 weight percent of the acrylic co-polymer.

The addition of the acrylic co-polymer creates a new product that is fast drying and has much higher durability than the original fingernail topcoat or fingernail lacquer, is very shiny and is easily removed with standard acetone or non-acetone based fingernail polish remover.

In an embodiment, the invention can provide a three part nail polish blend with an acrylic copolymer blend made from about 10 weight percent to about 40 weight percent of a crosslinked alkyl acrylic copolymer dissolved in 30 weight percent to 60 weight percent of a solvent based on a weight percent of the total acrylic polymer blend as the first part of the three part nail polish blend.

The crosslinked acrylic copolymer to solvent can be used in ratios of 500 grams to 1500 grams of crosslinked acrylic copolymer to 0.5 gallons to 1.5 gallons of solvent.

The second part of the three part nail polish blend can be a two component solvent formulation.

The first solvent component can have 65 weight percent to 75 weight percent of the total weight of the two component solvent formulation.

The first solvent component can have two ingredients: (i) 60 weight percent to 40 weight percent of an ethyl acetate based on a total weight percent of the first solvent component; and (ii) 40 weight percent to 60 weight percent of a butyl acetate based on the total weight percent of the first solvent component.

The second solvent component can have 25 weight percent to 35 weight percent of the total weight percent of the two component solvent formulation. The second solvent component can be an alcohol.

The third part of the three part nail polish blend can be a film-forming plasticizing mixture for adding to the two component solvent formulation. The film-forming plasticizing mixture can have two components.

The first component of the film forming plasticizing mixture can be 70 percent to about 90 percent by weight of a nitrocellulose based on the total weight percent of the film-forming plasticizing mixture. The nitrocellulose can create a nitrocellulose/acrylic copolymer matrix with ratios ranging from 20:1 to 5:1 of nitrocellulose to the crosslinked acrylic copolymer.

The second component of the film forming plasticizing mixture can be 10 weight percent to 30 weight percent of a plasticizer based on the weight percent of the total three part nail polish blend. The plasticizer can enter into interstices of the nitrocellulose/acrylic copolymer matrix modifying the flexibility of the nitrocellulose/acrylic copolymer matrix The three part nail polish blend can be combined in a ratio of 10:72:18 of acrylic copolymer blend: two component solvent formulation: film forming plasticizer mixture.

The three part nail polish blend can not only simultaneously dry the three part nail polish blend on a human fingernail in 1 minute to 2 minutes at ambient temperatures and pressures, and provide chip resistance and crack resistance for 2 to 3 weeks of normal wear; but can also dry additional wet layers of other nail polish, when applied as a top coat, producing a shiny long lasting chip resistant hard nail polish.

Unless otherwise stated, the following terms used in this application, including the specification and claims, have the definitions given below. It should be noted that, as used in the specification and the appended claims, the singular forms "a," "an" and "the" include plural referents unless the context clearly dictates otherwise. Definition of standard chemistry terms may be found in reference works. The practice of the present invention will employ, unless otherwise indicated, conventional methods of mass spectroscopy, protein chemistry, biochemistry, and pharmacology, within the skill of the art.

A benefit of this invention is that it reduces the risk to public health as it does not contain toluene, dibutyl phthalate, or formaldehyde, chemicals that are banned in the EU.

A further benefit of the invention is that it reduces the risk to public health in that it does not require the soaking of the fingernail in acetone or other fingernail polish removers to remove the polish or topcoat such as a UV gel requires. Soaking the fingers in chemicals such as these sends the solvents directly into the bloodstream and can lead to a detriment in a person's long term health due to acetone exposure.

Another benefit of the invention is that it can be used at a person's home and does not require special tools or UV lights. This is a further health benefit as exposure to UV light is known to cause skin cancer and the nails are actually the most vulnerable place to get cancer for most people.

Yet another benefit of the invention is that it is durable, lasting up to 3 weeks when properly applied. This is important as it reduces the economic expenditure of the average purchaser as the product doesn't need to be purchased or applied as often. Further, this will reduce the chemical impact on the environment as the product won't be used in as large a quantity as existing chemicals.

A benefit of the invention is that it dries in less than 2 minutes and dries all layers from the top layer down, a quality that no other polish or topcoat has.

The term "alkyl" means the monovalent branched or unbranched saturated hydrocarbon radical, consisting solely of carbon and hydrogen atoms, having from one to twelve carbon atoms inclusive, unless otherwise indicated. Examples of alkyl radicals can include, but are not limited to, methyl, ethyl, propyl, isopropyl, butyl, isobutyl, sec-butyl, tert-butyl, pentyl, n-hexyl, octyl, dodecyl, and the like.

The term "alkylene" as used herein means the divalent linear or branched saturated hydrocarbon radical, consisting solely of carbon and hydrogen atoms, having from one to eight carbon atoms inclusive, unless otherwise indicated. Examples of alkylene radicals can include, but are not limited to, methylene, ethylene, trimethylene, propylene, tetramethylene, pentamethylene, ethylethylene, and the like.

The term "alkenylene" means the divalent linear or branched unsaturated hydrocarbon radical, containing at least one double bond and having from two to eight carbon atoms inclusive, unless otherwise indicated. The alkenylene radical can include the cis or trans ((E) or (Z)) isomeric groups or mixtures thereof generated by the asymmetric carbons. Examples of alkenylene radicals can include, but are not limited to ethenylene, 2-propenylene, 1-propenylene, 2-butenyl, 2-pentenylene, and the like.

The term "aryl" means the monovalent monocyclic aromatic hydrocarbon radical consisting of one or more fused rings in which at least one ring is aromatic in nature, which can optionally be substituted with hydroxy, cyano, lower alkyl, lower alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals can include, but are not limited to, phenyl, naphthyl, biphenyl, indanyl, anthraquinolyl, and the like.

The term "halogen" as used herein refers to fluoro, bromo, chloro and/or iodo.

The term "acrylic copolymer(s)" as used herein means copolymers made using 1) alkyl methacrylate homo polymers, 2) polymers of alkyl methacrylates with other alkyl methacrylates or alkyl acrylates or other ethylenically unsaturated monomers, 3) alkyl acrylate homo polymers, and 4) alkyl acrylates with other alkyl acrylates or other ethylenically unsaturated monomers The components of the present invention are described below. Also included are non-limiting descriptions of the embodiments useful in the formulation of the present invention.

In embodiments, the three part nail polish blend can include from 0.25 weight percent to 1 weight percent of a suspension agent. In embodiments, the suspension agent can be fumed silica or bentonite clay.

In embodiments, the three part nail polish blend can include from 0.1 weight percent to 0.5 weight percent of a scent. In embodiments, the scent can be a lemon oil, lemon grass, a lavender oil, chamomile, or another citrus oil for enhanced aroma during application.

In embodiments, the three part nail polish blend can include from 0.1 weight percent to 5 weight percent of a pigment, a dye, or both the pigment and the dye, wherein the pigment and dye are non-toxic to humans.

In embodiments, the three part nail polish blend can use a crosslinked alkyl acrylic copolymer made of monomers of at least one of: methyl methacrylate and lauryl methacrylate.

In embodiments, the plasticizer can be at least one of: toluene sulfonamide formaldehyde resin, camphor, dibutyl phthalate, dioctyl phthalate, castor oil, tricresyl phophate, butyl phthalate, butyl glycolate, triphenyl phosphate, glyceryl tribenzoate benzyl benzoate, butyl stearate, triethyl citrate, and propylene glycol adipate.

In embodiments, the alcohol of the blend can be a polar aprotic solvent. The polar aprotic solvent can be an ester, an ethyl acetate, N,N-dimethylformamide, a butyl acetate and a xylene.

In embodiments, the three part nail polish blend can include 0.1 weight percent to 2 weight percent of a glitter with an emulsifying agent based on the total weight percent of the three part nail polish blend. In embodiments, the emulsifying agent can be fumed silica.

In embodiments, the three part nail polish blend can include 0.01 weight percent to 0.03 weight percent of an ultraviolet stabilizer. The ultraviolet stabilizer can be an ethyl-2-cyano-3,3-diphenylacrylate.

The invention also relates to a non-toxic to humans nail lacquer made from 5 weight percent to 17 weight percent of a nitrocellulose based on a total nail lacquer weight percentage;

1 weight percent to 3 weight percent of a crosslinked acrylic copolymer based on the total nail lacquer weight percentage with the crosslinked acrylic copolymer having a 1:1 ratio of methyl acrylates to lauryl acrylates, 0.5 weight percent to 2 weight percent of a toluene sulfonamide formaldehyde resin based on the total nail lacquer weight percentage; 1 weight percent to 3 weight percent of a plasticizer based on the total nail lacquer weight percentage; 50 weight percent to 70 weight percent of a solvent based on the total nail lacquer weight percentage; 0.01 weight percent to 1 weight percent of a UV stabilizer based on the total nail lacquer weight percentage; 0.25 weight percent to 1 weight percent of a suspension agent based on the total nail lacquer weight percentage; and 0.1 weight percent to 3 weight percent of a pigment or a dye based on the total nail lacquer weight percentage, which is non-toxic to humans.

In embodiments, the three part nail polish blend can also include an acrylic copolymer blend with 0.5 weight percent to 5 weight percent of a crosslinked alkyl acrylic copolymer based on a weight percent of the total formulation.

In embodiments, the first part of the three part nail polish blend can also include in addition to the crosslinked alkyl acrylic copolymer, 30 weight percent to 70 weight percent by weight of a solvent based on a weight percent of a total weight of the acrylic copolymer. The crosslinked acrylic copolymer can be in amounts that range from 500 grams to 1500 grams. When 500 to 1500 grams of acrylic copolymer are used, the solvent can be used in amounts ranging from 0.5 gallons to 1.5 gallons.

In embodiments, the nitrocellulose can blend with the acrylic copolymer creating a unique matrix of the nitrocellulose in between the chains of acrylic copolymer, nested in the interstices of the polymer. The nitrocellulose blends to acrylic copolymer can used in ratios of 20:1 to 10:1. In embodiments, the ratio of nitrocellulose to acrylic copolymer can be 5:1.

Like the nitrocellulose, the plasticizer can also enter into interstices of the acrylic copolymer modifying the flexibility of the formed nitrocellulose/acrylic copolymer matrix.

In embodiments, the three part nail polish blend can be blended in a ratio of 10:72:18 to produce the nail polish composition that when applied to a nail dries in less than 2 minutes at ambient temperatures and pressures and has chip resistance and cracking resistance for up to 3 weeks of normal wear and when the nail polish composition is applied to wet layers of other nail polish, the nail polish composition dries all layers simultaneously producing a shiny long lasting chip resistant hard nail polish.

In an embodiment, the compositions of the invention can comprise a copolymer. The copolymer can have a molecular weight that is greater than about 2,000 daltons (Da).

In embodiments, the composition of the invention can comprise a copolymer which can have a molecular weight ranging from 2,000 daltons (Da) to about 250,000 daltons (Da).

In an embodiment, the copolymer can be an acrylic copolymer, such as a methyacrylate. The (meth)acrylic copolymers can comprise about 80 to about 99.8 parts by weight of alkyl acrylic acid ester monomers having from about 2 to about 14 carbon atoms of alkyl group.

The alkyl acrylic acid ester monomers usable herein can have from 2 to 14 carbon atoms of alkyl group and may be ethyl(meth)acrylate, n-propyl(meth)acrylate, isopropyl (meth)acrylate, n-butyl(meth)acrylate, t-butyl(meth)acrylate, sec-butyl(meth)acrylate, pentyl(meth)acrylate, 2-ethylhexyl(meth)acrylate, n-octyl(meth)acrylate, isooctyl(meth) acrylate, isononyl(meth)acrylate, lauryl(meth)acrylate, and tetradecyl(meth)acrylate.

Examples of acrylate copolymers can be formed from monomers including alkyl acrylates such as methyl acrylate, ethyl acrylate, propyl acrylate, butyl acrylate, pentyl acrylate, hexyl acrylate, 2-ethylhexyl acrylate, octyl acrylate, nonyl acrylate, decyl acrylate and dodecyl acrylate; alkoxyalkyl acrylates such as methoxyethyl acrylate, ethoxyethyl acrylate, propoxyethyl acrylate, butoxyethyl acrylate and ethoxypropyl acrylate; alkyl methacrylates such as methyl methacrylate, ethyl methacrylate, propyl methacrylate, butyl methacrylate, pentyl methacrylate, hexyl methacrylate, 2-ethylhexyl methacrylate, octyl methacrylate, nonyl methacrylate, decyl methacrylate and dodecyl methacrylate; alkoxyalkyl methacrylates such as methoxyethyl methacrylate, ethoxyethyl methacrylate, propoxyethyl methacrylate, butoxyethyl methacrylate and ethoxypropyl methacrylate; (poly)alkylene glycol diacrylates such as ethylene glycol diacrylate, diethylene glycol diacrylate, triethylene glycol diacrylate, poly(ethylene glycol) diacrylate, propylene glycol diacrylate, dipropylene glycol diacrylate and tripropylene glycol diacrylate; polyvalent acrylates such as trimethylolpropane triacrylate; polyvalent methacrylates such as trimethylolpropane trimethacrylate; acrylates of alicyclic alcohols such as cyclohexyl acrylate; methacrylates of alicyclic alcohols such as cyclohexyl methacrylate; and fluorine-substituted alkyl methacrylates and fluorine-substituted alkyl acrylates.

These acrylate monomers can be used alone or in combination. These acrylate monomers can be liquid, solid, or gaseous under the reaction conditions. For ease of operation, liquid monomers are preferably used in reactions.

An acrylic copolymer according to the present invention can be formed by the copolymerization of acrylic monomers described above. The acrylic monomers can have functional groups so that the acrylic monomers can react with a crosslinker. Alternatively, the acrylic polymer of the present invention can be obtained from a commercial source.

Commercially available examples of acrylic copolymers for use in the present invention can include, but are not limited to, ELVACITE® 2041, ELVACITE® 2014 ELVACITE® 2552, and ELVACITE® 2552C which can be obtained from Lucite International, Inc. Texas and INEOS Acrylics of Cordova, Tenn.; and Br85, manufactured by Dianal America, Inc. of Pasadena, Tex.

The acrylic copolymer can be dissolved in an organic solvent. The organic solvent can be any organic solvent, such as for example, methyl acetate, ethyl acetate, propyl acetate, isopropyl actate, butyl acetate, isobutyl acetate, tert-butyl acetate, pentane, hexane, heptane, acetone, methyl ethyl ketone, xylene, and the like, and combinations thereof.

In one aspect of the invention, the organic solvent can be an alkyl ester. The alkyl group can have from 1 to 14 carbons. Examples of alkyl group can include, but are not limited to, methyl, ethyl, n-propyl, isopropyl, isobutyl, sec-butyl, tert-butyl, pentyl, n-hexyl, octyl, dodecyl, and the like. The acid can be acetic acid, benzoic acid, butyric acid, capric acid, caproic acid, caprylic acid, citric acid, formic acid, fumaric acid, gluconic acid, glyceric acid, glycolic acid, heptanoic acid, lactic acid, lauric acid, linoleic acid, maleic acid, malic acid, myristic acid, nonanoic acid, oleic acid, palmitic acid, propionic acid, salicyclic acid, sorbic acid, stearic acid, tartaric acid, undacanoic acid, undecylenic acid and valeric acid. The acid can be acetic acid, citric acid, lactic acid or lauric acid.

In embodiments, the compositions of the invention can include the crosslinked acrylic copolymer dissolved in the solvent in a ratio of about 1:100 to about 100:1 by weight.

The nail polish compositions of the invention can be formulated as a clear, colorless lacquer component optionally mixed with a pigment component when a colored polish is desired. Also included in embodiments, are drying accelerators, a thixotropic agent, a brightening agent, and aromatic ketones.

In an embodiment, the nail polish lacquer can include about 0.1 percent to about 60 percent of the acrylic copolymer dissolved in an organic solvent; about 5 percent to about 40 percent, of a film-forming polymer; about 0.1 percent to about 10 percent, of a plasticizer; and about 5 percent to about 80 percent of a solvent system.

The nail polish lacquer of the invention can optionally contain a gelling agent, such as about 0.2 percent to about 0.4 percent of least one thixotropic agent, a drying accelerator, a suspension agent, a UV inhibitor, pigments and dyes, and the like, wherein the above percentages are based on the total weight of the lacquer component. In embodiments, the final fingernail lacquer can contain from about 0.5 weight percent to about 10 weight percent of the acrylic co-polymer.

A first example of an embodiment of the invention is a fingernail lacquer composition according to the table below:

| Component | Weight % |
| --- | --- |
| Nitrocellulose | 20.00 |
| Acrylic Copolymer Granules In Ethyl Acetate | 10.00 |
| Isopropyl Alcohol - Second Solvent Component | 5.00 |
| Camphor Plasticizer | 1.00 |
| Butyl Acetate - First Solvent Component | 28.20 |
| Ethyl Acetate - First Solvent Component | 31.99 |
| Ethyl-2-cyano-3,3-diphenylacrylate | 0.01 |
| Fuming Silica | 0.50 |
| Titanium Dioxide | 2.50 |
| Lemon Oil | 0.30 |
| Glitter With Emulsifying Agent | 0.50 |
| TOTAL | 100.00 |

The physical properties of this example have hardness of 15.5 as determined by a TUKON™ 2500 Knoop/Vickers Automated Hardness Tester.

The specific gravity of this example is 1.1. The viscosity when liquid for this example is 1500 centipoise (CPS).

Upon additional testing it is expected that this formulation, once hardened on a nail, will have chip resistance and crack resistance for up to 3 weeks of normal wear.

This formulation of this example can dry additional wet layers of other nail polish, when applied as a top coat, producing a shiny long lasting chip resistant hard nail polish.

This formulation can dry the entire three part nail polish blend in 1 minute to 2 minutes at ambient temperatures and pressures.

A second example of an embodiment of the invention is a fingernail lacquer composition according to the table below:

| Component | Weight % |
| --- | --- |
| Nitrocellulose | 19.40 |
| Acrylic Copolymer Granules | 10.00 |
| Acetyl Tributyl Citrate Plasticizer | 2.90 |
| Butyl Acetate - First Solvent Component | 26.92 |
| Ethyl Acetate - First Solvent Component | 32.75 |
| Propanol - Second Solvent Component | 5.00 |
| Ethyl-2-cyano-3,3-diphenylacrylate | 0.03 |
| Titanium Dioxide | 3.00 |
| TOTAL | 100.00 |

The physical properties of this second composition have a hardness of 15.5 as determined by a TUKON™ 2500 Knoop/Vickers Automated Hardness Tester.

The specific gravity of this example is 1.07. The viscosity when liquid for this example is 1500 centipoise (CPS).

Upon additional testing it is expected that this formulation, once hardened on a nail will have chip resistance and crack resistance for up to 3 weeks of normal wear.

This formulation of this example can dry additional wet layers of other nail polish, when applied as a top coat, producing a shiny long lasting chip resistant hard nail polish.

This formulation can dry the entire three part nail polish blend in 1 to 2 minutes at ambient temperatures and pressures.

A third example of an embodiment of the invention is a fingernail lacquer composition according to the table below:

| Component | Weight % |
| --- | --- |
| Nitrocellulose | 20.00 |
| Acrylic Copolymer Granules In Ethyl Acetate | 10.00 |
| Ethyl Alcohol - Second Solvent Component | 5.00 |
| Acetyl Tributyl Citrate Plasticizer | 3.00 |
| Butyl Acetate - First Solvent Component | 28.98 |
| Ethyl Acetate - First Solvent Component | 32.99 |
| Ethyl-2-cyano-3,3-diphenylacrylate | 0.03 |
| TOTAL | 100.00 |

The physical properties of this third composition have hardness of 15.5 as determined by a TUKON™ 2500 Knoop/Vickers Automated Hardness Tester.

The specific gravity of this example is 1.05. The viscosity when liquid for this example is 1500 centipoise (CPS).

The composition of the present invention can be made using conventional formulation and mixing techniques.

Upon additional testing it is expected that this formulation, once hardened on a nail will have chip resistance and crack resistance for up to 3 weeks of normal wear.

This formulation of this example can dry additional wet layers of other nail polish, when applied as a top coat, producing a shiny long lasting chip resistant hard nail polish.

This formulation can dry the entire three part nail polish blend in 1 minute to 2 minutes at ambient temperatures and pressures.

A usable formulation was composed by mixing 35 weight percent Lucite ELVACITE® Resin 2552C with 65 percent Ethyl Acetate and adding the resulting mixture to a generic fingernail topcoat or fingernail lacquer to create a mixture that contains from 0.5 weight percent to 10 weight percent acrylic co-polymer.

The compositions of the invention can contain polar aprotic solvents, such as, for example, esters, ethyl acetate, N,N-dimethylformamide, xylene, and the like. The compositions do not contain substantial amounts of a solvent or an excipient that is highly polar and/or protic.

For example, solvents with polarities that approach water are not included in the compositions of the invention. Such solvents, include, for example alcohols, such as methanol, ethanol, propanol, isopropanol, butanol, isobutanol, tert-butanol, and the like.

The compositions can contain an alcohol that is less than about 5 percent by total weight, less than about 7 percent by total weight, less than about 8 percent by total weight, less than about 9 percent by total weight, less than about 10 percent by total weight, less than about 11 percent by total weight, less than about 12 percent by total weight, and the like. The higher concentration of an alcohol can result in the acrylic polymer, such as the dodecyl methacrylate-methyl methacrylate polymer to precipitate from the composition and the resultant composition can appear cloudy.

The use of the nail lacquer and fingernail topcoat is as follows:

The fingernail can be thoroughly cleaned to remove all oil from the nail.

A base-coat nail lacquer can be applied to the fingernail to promote proper adhesion of the nail lacquer to the fingernail. Wait until the base-coat has properly dried before applying the following fingernail lacquer coat. Fingernail lacquer can be applied to the fingernail over the base coat. Two coats can be applied for some colors for even color distribution. Wait until the fingernail lacquer is properly dry before applying the next coat. One or two layers of fingernail top coat can be applied over the top of the fingernail lacquer. Wait until the first coat is properly dry before applying the next coat.

The lacquer of the invention, when applied to the nail, can dry in an ambient atmosphere is less than about 7 minutes.

The compositions of the invention are durable and typically do not chip or crack for a period of at least about three days of wearing on a human or synthetic nail. Coatings formed of the lacquer component per se, as well as the coatings formed from compositions which include both the lacquer and pigment components, exhibit an acceptable gloss.

The lacquer of the invention, when applied to the nail, can last for at least two weeks and up to at least three weeks. The lacquer can then be reapplied, or the previous layer(s) can be removed, and new layer applied.

The lacquer of the invention can be removed from nails using standard nail polish removers or an organic solvent, such as acetone.

The fast drying topcoat or nail lacquer is long lasting, has a high gloss, and can be removed by nail polish remover.

An alternative formulation would be to replace the dodecyl methacrylate-methyl methacrylate polymer or ELVACITE® 2552C resin with film-forming water-insoluble polymers selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

In other embodiments, thedodecyl methacrylate-methyl methacrylate polymer or ELVACITE®2552C resin can be replaced with film-forming water-insoluble polymers selected from the group consisting of, polyacryls, polymethacryls, polystyrene-polyacryl mixtures, styrene-acryl copolymers, and mixtures thereof.

An embodiment would use as plastizers: dibutyl phthalate, camphor, dioctyl phthalate, castor oil, tricresyl phophate, butyl phthalate, butyl glycolate, triphenyl phosphate, glyceryl tribenzoate benzyl benzoate, butyl stearate, triethyl citrate, propylene glycol adipate for flexibility and chip resistance.

Another embodiment of the invention can include glitter added to the fingernail lacquer or fingernail topcoat formulation to form a fingernail glitter that has the same properties of new fingernail lacquer or fingernail topcoat formulation. The glitter can require the addition of a small amount of suspension to keep the glitter from collecting on the bottom or the top of the nail coating bottle.

Another embodiment of the invention can include nonessential components such as preservatives, vitamins, herbal extracts, FDC acceptable dyes, moisturizing agents and so on added to the fingernail lacquer.

Another embodiment can include adding aromatic agents to the formulation, such as lavender, lemon and citrus oil in amounts from 0.1 weight percent to 0.5 weight percent based on the total formulation.

In another aspect of the invention, the compositions can optionally contain aromatic ketones. Exemplary aromatic ketones useful in the pigment component can include 2,2-dimethoxy-2-phenyl acetophenone, 1-hydroxy cyclohexyl phenyl ketone, 2-hydroxy-2-methyl-1-phenyl-propane-1-one and 2,4,6-trimethyl benzoldiphenyl.

In another embodiment of the invention, the composition can be a non-toxic to humans nail lacquer comprising 5 weight percent to 17 weight percent of a nitrocellulose based on a total nail lacquer, 1 weight percent to 3 weight percent of an acrylic copolymer comprising a 1:1 ratio of methyl to lauryl acrylates based on the total nail lacquer, 0.5 weight percent to 2 weight percent of a toluene sulfonamide formaldehyde resin based on the total nail lacquer, 1 weight percent to 3 weight percent of a plasticizer based on the total nail lacquer, 50 weight percent to 70 weight percent of a solvent based on the total nail lacquer, 0.01 weight percent to 1 weight percent of a UV stabilizer based on the total nail lacquer, 0.25 weight percent to 1 weight percent of a suspension agent based on the total nail lacquer, and 0.1 weight percent to 3 weight percent of a pigment or a dye based on the total nail lacquer, which is non-toxic to humans.

While these embodiments have been described with emphasis on the embodiments, it should be understood that within the scope of the appended claims, the embodiments might be practiced other than as specifically described herein.

What is claimed is:

1. A nail polish composition with a three part nail polish blend, wherein the three part nail polish blend comprises:
 a) an acrylic copolymer blend comprising:
  (i) 10 weight percent to 40 weight percent of a crosslinked alkyl acrylic copolymer based on a weight percent of the acrylic copolymer blend; and
  (ii) 30 weight percent to 60 weight percent of a solvent based on a weight percent of the acrylic copolymer blend, wherein the crosslinked acrylic copolymer to the solvent is used in ratios of 500 grams to 1500 grams of the acrylic copolymer to 0.5 gallons to 1.5 gallons of the solvent;
 b) a two component solvent formulation comprising:
  (i) 65 weight percent to 75 weight percent of a first solvent component based on the total weight percent of the two component solvent formulation, wherein the first solvent component comprises:
   1) 60 weight percent to 40 weight percent of an ethyl acetate based on a total weight percent of the first solvent component; and
   2) 40 weight percent to 60 weight percent of a butyl acetate based on the total weight percent of the first solvent component;
  (ii) 25 weight percent to 35 weight percent of a second solvent component based on the total weight percent of the two component solvent formulation, wherein the second solvent component comprises an alcohol; and
 c) a film forming plasticizing mixture for addition to the two component solvent formulation, wherein the film forming plasticizing mixture comprises:
  (i) 70 weight percent to 90 weight percent of a nitrocellulose based on the total weight percent of the film-forming plasticizing mixture to form a nitrocellulose/acrylic copolymer matrix with ratios ranging from 20:1 to 5:1 weight percent based on the total weight of the film forming plasticizing mixture of the nitrocellulose to the crosslinked acrylic copolymer; and
(ii) 10 weight percent to 30 weight percent of a plasticizer based on the weight percent of the total nail polish blend, wherein the plasticizer enters into interstices of the nitrocellulose/acrylic copolymer matrix modifying the flexibility of the nitrocellulose/acrylic copolymer matrix; and
wherein the nail polish composition comprises the acrylic copolymer blend, the two component solvent formulation, and the film forming plasticizer mixture at a weight ratio of 10:72:18, and further wherein the nail polish composition simultaneously:
(i) dries in 1 minute to 2 minutes at ambient temperatures and pressures, with chip resistance and crack resistance for 2 weeks to 3 weeks of normal wear; and
(ii) dries additional wet layers of other nail polish, when the nail polish composition is applied as a top coat, producing a shiny chip resistant hard nail polish.

2. The nail polish composition of claim 1, further comprising from 0.25 weight percent to 1 weight percent of a suspension agent.

3. The nail polish composition of claim 2, wherein the suspension agent is fumed silica or bentonite clay.

4. The nail polish composition of claim 1, further comprising from 0.1 weight percent to 0.5 weight percent of a scent.

5. The nail polish composition of claim 4, wherein the scent is selected from the group consisting of: a lemon oil, lemon grass, a lavender oil, chamomile, or another citrus oil for enhanced aroma during application.

6. The nail polish composition of claim 1, further comprising from 0.1 weight percent to 5 weight percent of a pigment, a dye, or both, wherein the pigment or the dye is non-toxic to humans.

7. The nail polish composition of claim 1, wherein the crosslinked alkyl acrylic copolymer consists of monomers of at least one of: methyl methacrylate and lauryl methacrylate.

8. The nail polish composition of claim 1, wherein the plasticizer is at least one of: toluene sulfonamide formaldehyde resin, camphor, dibutyl phthalate, dioctyl phthalate, castor oil, tricresyl phophate, butyl phthalate, butyl glycolate, triphenyl phosphate, glyceryl tribenzoate benzyl benzoate, butyl stearate, triethyl citrate, and propylene glycol adipate.

9. The nail polish composition of claim 1, comprising from 0.1 weight percent to 2 weight percent of a glitter with an emulsifying agent based on the total weight percent of the three part nail polish blend.

10. The nail polish composition of claim 9, wherein the emulsifying agent is fumed silica.

11. The nail polish composition of claim 1, comprising from 0.01 weight percent to 0.03 weight percent an ultraviolet stabilizer.

12. The nail polish composition of claim 11, wherein the ultraviolet stabilizer is an ethyl-2-cyano-3,3-diphenylacrylate.

13. A nail polish composition with a three part nail polish blend, wherein the three part nail polish blend comprises:
a) an acrylic copolymer blend comprising:
(i) 10 weight percent to 40 weight percent of a crosslinked alkyl acrylic copolymer based on a weight percent of the acrylic copolymer blend; and
(ii) 30 weight percent to 60 weight percent of a solvent based on a weight percent of the acrylic copolymer blend, wherein the crosslinked acrylic copolymer to the solvent is used in ratios of 500 grams to 1500 grams of the acrylic copolymer to 0.5 gallons to 1.5 gallons of the solvent;

b) a two component solvent formulation comprising:
(i) 65 weight percent to 75 weight percent of a first solvent component based on the total weight percent of the two component solvent formulation, wherein the first solvent component comprises:
1) 60 weight percent to 40 weight percent of an ethyl acetate based on a total weight percent of the first solvent component; and
2) 40 weight percent to 60 weight percent of a butyl acetate based on the total weight percent of the first solvent component;
(ii) 25 weight percent to 35 weight percent of a second solvent component based on the total weight percent of the two component solvent formulation, wherein the second solvent component comprises a polar aprotic solvent; and
c) a film forming plasticizing mixture for addition to the two component solvent formulation, wherein the film forming plasticizing mixture comprises:
(i) 70 weight percent to 90 weight percent of a nitrocellulose based on the total weight percent of the film-forming plasticizing mixture to form a nitrocellulose/acrylic copolymer matrix with ratios ranging from 20:1 to 5:1 weight percent based on the total weight of the film forming plasticizing mixture of the nitrocellulose to the crosslinked acrylic copolymer; and
(ii) 10 weight percent to 30 weight percent of a plasticizer based on the weight percent of the total nail polish blend, wherein the plasticizer enters into interstices of the nitrocellulose/acrylic copolymer matrix modifying the flexibility of the nitrocellulose/acrylic copolymer matrix; and
wherein the nail polish composition comprises the acrylic copolymer blend, the two component solvent formulation, and the film forming plasticizer mixture at a weight ratio of 10:72:18, and further wherein the nail polish composition simultaneously:
(i) dries in 1 minute to 2 minutes at ambient temperatures and pressures, with chip resistance and crack resistance for 2 weeks to 3 weeks of normal wear; and
(ii) dries additional wet layers of other nail polish, when the nail polish composition is applied as a top coat, producing a shiny chip resistant hard nail polish.

14. The nail polish composition of claim 13, wherein the polar aprotic solvent is a member of the group consisting of: ester, ethyl acetate, N,N-dimethylformamide, butyl acetate and xylene.

15. A non-toxic to humans nail lacquer comprising:
a) 5 weight percent to 17 weight percent of a nitrocellulose based on a total nail lacquer weight percentage;
b) 1 weight percent to 3 weight percent of a crosslinked acrylic copolymer comprising a 1:1 ratio of methyl to lauryl acrylates based on the total nail lacquer weight percentage;
c) 0.5 weight percent to 2 weight percent of a toluene sulfonamide formaldehyde resin based on the total nail lacquer weight percentage;
d) 1 weight percent to 3 weight percent of a plasticizer based on the total nail lacquer weight percentage;
e) 50 weight percent to 70 weight percent of a solvent based on the total nail lacquer weight percentage;
f) 0.01 weight percent to 1 weight percent of a UV stabilizer based on the total nail lacquer weight percentage;
g) 0.25 weight percent to 1 weight percent of a suspension agent based on the total nail lacquer weight percentage; and h) 0.1 weight percent to 3 weight percent of a pigment or a dye based on the total nail lacquer weight percentage, which is non-toxic to humans.

* * * * *